United States Patent
Lee et al.

(10) Patent No.: US 8,024,135 B2
(45) Date of Patent: Sep. 20, 2011

(54) ULTRAVIOLET LIDAR FOR DETECTION OF BIOLOGICAL WARFARE AGENTS

(75) Inventors: Hyo Sang Lee, Silver Spring, MD (US); Coorg R. Prasad, Silver Spring, MD (US)

(73) Assignee: Science & Engineering Services, Inc., Columbia, MD (US)

( * ) Notice: Subject to any disclaimer, the term of this patent is extended or adjusted under 35 U.S.C. 154(b) by 693 days.

(21) Appl. No.: 11/104,505

(22) Filed: Apr. 13, 2005

(65) Prior Publication Data

US 2010/0006760 A1    Jan. 14, 2010

Related U.S. Application Data

(60) Provisional application No. 60/561,538, filed on Apr. 13, 2004.

(51) Int. Cl.
*G01N 21/64* (2006.01)
(52) U.S. Cl. .......................... 702/40; 356/4.01
(58) Field of Classification Search .................. None
See application file for complete search history.

(56) References Cited

U.S. PATENT DOCUMENTS 6,593,582 B2    7/2003    Lee et al.
2002/0175294 A1*    11/2002    Lee et al. .................. 250/458.1

OTHER PUBLICATIONS

Snook, "Laser techniques for chemical analysis," Chemical Society Review, vol. 26 (1997) pp. 319-326.*
Gittins et al., "Quantitative Gas Sensing by Backscatter-Absorption Measurement of a Pseudo-Random Code Modulated 8 micrometer Quantum Cascase Laser," Optics Letters, vol. 25 (2000) pp. 1162-1164.*
U.S. Appl. No. 11/281,621, filed Nov. 18, 2005, Lee et al.
U.S. Appl. No. 12/644,881, filed Dec. 22, 2009, Prasad, et al.

* cited by examiner

*Primary Examiner* — Marjorie Moran
*Assistant Examiner* — Anna Skibinsky
(74) *Attorney, Agent, or Firm* — Oblon, Spivak, McClelland, Maier & Neustadt, L.L.P.

(57) ABSTRACT

A system and method for detecting airborne agents. The system includes a semiconductor ultraviolet optical source configured to emit an ultraviolet light, a controller configured to generate a pseudo-random code for emission of the ultraviolet light modulated at the pseudo-random code, a telescope configured to focus the ultraviolet light to a distance from the source and to receive elastically backscattered signals and fluorescence signals from the distance, and a sensor configured to detect the elastically backscattered and fluorescence signals. The method generates a pseudo-random code and emits at least one wavelength of ultraviolet light modulated at the pseudo-random code, transmits the modulated ultraviolet light pulses to a distance from the source, receives elastically backscattered signals and fluorescence signals from the distance, and detects the elastically backscattered and fluorescence signals.

25 Claims, 10 Drawing Sheets
(8 of 10 Drawing Sheet(s) Filed in Color)

ULTRAVIOLET LIDAR FOR DETECTION OF BIOLOGICAL WARFARE AGENTS

CROSS REFERENCE TO RELATED APPLICATIONS

This application is related to and claims priority to U.S. Application No. 60/561,538 filed on Apr. 13, 2004, the entire contents of which are incorporated herein by reference.

DISCUSSION OF THE BACKGROUND

1. Field of the Invention

This invention relates in general to laser induced detecting and ranging (LIDAR) systems.

2. Background of the Invention

Current methods for bio-warfare agent (BWA) sensing rely on point detectors, where a local sample is taken—either in the form of air sampler or a swab—and analyzed. The analysis can be based on immuno-assay, culture, or even a fluorescence based aerosol particle sizer or detector. A stand-off detector does not need to bring the sample to it for analysis, and is thus able to provide advance warning even before the BW agent arrives near the sensor, and operates continuously—not batch processing.

Stand-off sensors for the detection and discrimination of bio-warfare agent aerosols have been used for performing the task of round-the-clock surveillance to provide advance warning for personnel of the release of a BWA. A fluorescence lidar, which first detects aerosol particles by elastic light scattering and then employs UV laser excitation to generate auto-fluorescence from the proteins contained in the BWA particles for discrimination, is well established as a technique of choice for the stand-off BWA sensor. Although fluorescence sensors are not capable of specific identification, their real-time capability for standoff and point detection and discrimination with low false alarm rates makes them well suited as the first sensor in a suite of sensors.

However, such UV fluorescence lidars have conventionally required a large, high energy UV laser source and are consequently bulky, and expensive, which in turn have limited the utility of standoff lidar sensors. Indeed, in view of the small fluorescence cross sections for most of the BW agents, fluorescence lidars have relied upon high peak power (multi kW) pulsed solid state UV lasers to generate sufficient fluorescence signal from BW agent aerosols to achieve adequate measurement range and sensitivity.

Thus, the size, cost, and limited utility of UV laser sources have limited the application of UV laser sources in lidar sensor applications.

SUMMARY OF THE INVENTION

One object of at least one embodiment of the present invention is to provide a system and method for lidar detection which can utilize the recent availability of semiconductor ultraviolet optical source (SUVOS) semiconductor UV laser diodes.

Another object of an embodiment of the present invention is to provide a compact stand-off BW sensor that can be widely deployed.

Another object of an embodiment of the present invention is to provide miniature sensor systems which can be mounted on robotic air-borne and ground vehicles thereby enhancing the BWA detection capability.

Various of these and other objects are provided by the present invention in a novel system and method for detecting airborne agents. In a preferred embodiment, the system The system includes a semiconductor ultraviolet optical source configured to emit an ultraviolet light, a controller configured to generate a pseudo-random code for emission of the ultraviolet light modulated at the pseudo-random code, a telescope configured to focus the ultraviolet light to a distance from the source and to receive elastically backscattered signals and fluorescence signals from the distance, and a sensor configured to detect the elastically backscattered and fluorescence signals. The method according to one embodiment of the present invention generates a pseudo-random code and emits at least one wavelength of ultraviolet light modulated at the pseudo-random code, transmits the modulated ultraviolet light pulses to a distance from the source, receives elastically backscattered signals and fluorescence signals from the distance, and detects the elastically backscattered and fluorescence signals.

Several orders of magnitude reduction in cost, size and complexity of the BWA sensors can be expected to result from certain embodiments of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee. A more complete appreciation of the present invention and many attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
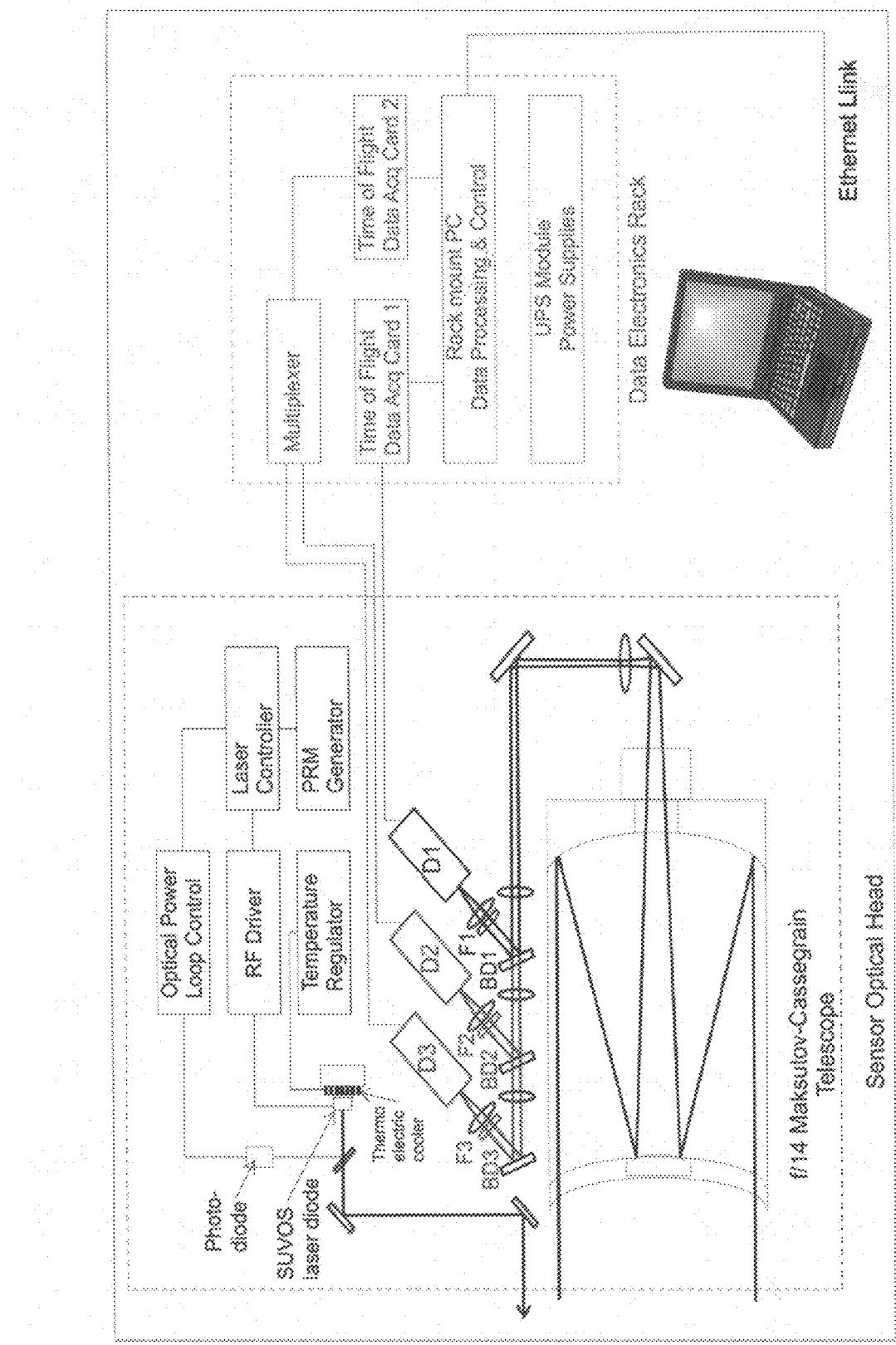
FIG. 1 is an optical and electronic system layout of a UV biological trigger lidar breadboard sensor of a preferred embodiment of the present invention.

A direct replacement of the pulsed solid state UV laser by the low power UV laser diodes would drastically reduce the range capability and sensitivity of such a lidar. However, in comparison with pulsed solid state lasers, semiconductor UV laser diodes are low power continuous-wave (cw) or pulsed devices with output powers of the order of tens of mW. However by taking advantage of pseudo random modulation (PRM), adequate sensitivity and range performance for the lidar system of the present invention are expected even at 10 mW power level of UV laser diodes. Accordingly, the present invention can realize a practical semiconductor ultraviolet optical source (SUVOS) for a BWA stand-off sensor.

In a conventional lidar technique, a short laser pulse is transmitted into the atmosphere, and a range resolved lidar profile is generated by time gating the signal backscattered by the aerosol and molecular components present in the beam path. On the other hand, in the PRM lidar, a cw laser is utilized, and its output is amplitude modulated by a continuously repeating PR code (e.g., the A code or the M code) of a fixed length. The pseudo-random code can be based on a cyclic, digital (1 or 0) Nth order PR code. The M-code refers to maximum-length pseudo-random digital sequence (i.e., a sequence composed of ones and zeros) and usually generated by shift register by known procedures. "A" codes were introduced to avoid a common problem with the M-code, where the number of ones always exceeds the number of zeros by one, and thus includes the background noise in the correlation. See Y. Emery and C. Flesia, "Use of A1 and A2 sequences to modulate continuous-wave pseudorandom noise lidar", Applied Optics, 37, 12, 2238-2242, 1998, the entire contents of which are incorporated herein by reference.

The PRM correlation method in general uses the delta function property of the autocorrelation function of a pseudo-random code. In one embodiment, the output of a laser is modulated by a maximal sequence PRM code produced by a PRM generator. The fluorescence signal from a sample is then digitized for example with a low bit resolution and averaged for a number of cycles of the PRM sequence. Cross correlations of this signal with the original transmitter code can then be calculated, which cover the entire code length. Due to the delta function property of the PRM code, the cross correlation is expected to be zero except in the case of a null phase difference between the transmitted code and the received code. A null phase difference is realized for the time shift corresponding to the time delay of the fluorescence signal from the excitation laser modulation. Accordingly, the correlation values for a fluorescence signal decaying exponentially with a time constant of $\tau$ is expected to have a similar exponential decay as the fluorescence intensity decay; thus, the correlation decay is expected to be a direct replica of the fluorescence intensity decay.

Accordingly, one property of a PR modulated signal is that its autocorrelation yields an approximate delta function profile. This property permits a range resolved lidar profile to be constructed by correlating the lidar signal with the PR code, with the correlation time delay corresponding to the round trip time to the object and the correlation amplitude corresponding to the lidar signal strength.

Cross-correlation and autocorrelation of two signals or waveforms are well known techniques, as described for example in S. Hoykin, "Digital Communications" John Wiley, 1988, and by Lee et al in U.S. Pat. No. 5,737,077, the entire contents of which are incorporated herein by reference. PRM technology as applied in the present invention is thus uniquely suited for the BW agent stand-off sensor, owing to PRM to utilize a cw light source for range resolved measurements. Further, PRM has a high sensitivity, due to the phase sensitive detection characteristics thereof.

Moreover, in a pulsed laser with large peak power and short pulse duration, the average output power can be comparable to a semiconductor laser diode. For example a micro-chip laser with a 1 µJ/pulse, 1 ns pulse duration and 10 kHz pulse repetition frequency, corresponds to 1 kW peak power, but the average power is 10 mW. Since the PRM lidar technique of the present invention permits continuous measurement, it in effect allows a low average power source to function as effectively as a high peak power pulsed laser.

In one embodiment of the present invention, the ultraviolet lidar sensor of the present invention employs a low-power (~5 mW), continuous-wave, 375 nm semiconductor laser diode that was modulated at high-speed with a pseudo-random (PR) code to provide range-resolved lidar detection of both aerosol elastic scattering and fluorescence. The sensor incorporates a 150 mm diameter receiver telescope and 3 photon-counting detection channels centered at 375 nm, 440 nm, and 550 nm. Aerosol elastic and fluorescence lidar profiles were obtained by correlating the signal photon-counts with the PR code. Demonstrations of the present invention have detected stimulants at a lidar range of 7.5 m, and in one embodiment of the present invention stimulants have been detected at a lidar range of several hundred meters, using a continuously scanned (±13°) LIDAR in a horizontal plane to detect downwind stimulant and interferent aerosol disseminations.

Referring now to the drawings, wherein like reference numerals designate identical, or corresponding parts throughout the several views, and more particularly to FIG. 1, FIG. 1 shows an optical and electronic system layout of one PRM lidar breadboard according to a preferred embodiment of the present invention, hereinafter referred to as UBTL (Ultraviolet Biological Trigger Lidar), because of its application as a front-end trigger sensor for other point sensors.

A 375 nm laser diode supplied by CREE™ constituted the active optical source component of the lidar system of the present invention. The 375 nm laser diode was packaged on a standard TO-9 semiconductor diode header without a cover or window. The peak power output of the 375 nm laser diodes was about 10 mW. A compact thermoelectrically cooled mount maintained the temperature of the laser constant throughout the experiments. The laser diode mount was also furnished with a fused silica aspheric lens for collimating the output. A high speed laser diode current driver was used to supply the current and also to modulate its output. The output power of the diode was found to decrease gradually due to aging. The threshold voltage of the diode also correspondingly increased. A laser control circuit of the present invention is configured to maintain the laser power output nearly constant, by monitoring the laser output power by a photodiode and increasing the driver output voltage.

Figure 2:
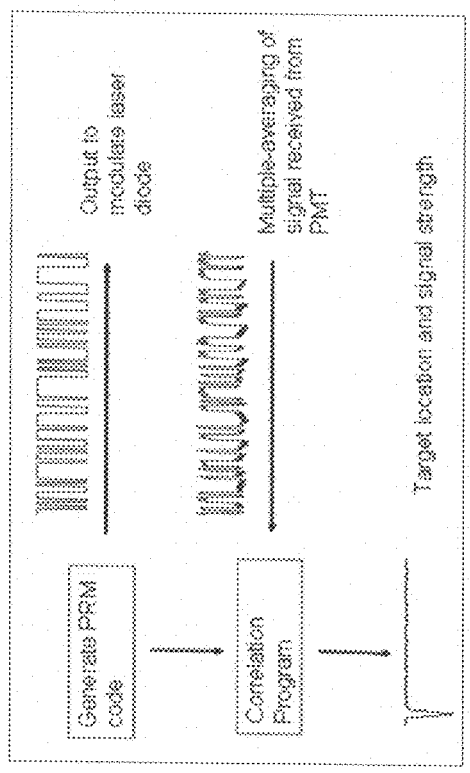
FIG. 2 depicts lidar profiles, i.e., aerosol backscatter signal vs. range profiles, obtained with a preferred embodiment of the present invention by cross correlating the received signal with a pseudo-random modulation code applied to the broadcast signals.

A pseudo-random generator can be a deterministic algorithm that generates a sequence of numbers with little or no discernible pattern in the numbers, except for broad statistical patterns. Deterministic algorithms are known in the art. In one embodiment of the present invention, a PR code generator (e.g., an FPGA Field Programmable Gate Array on for example a programmable logic (TTL) IC chip) supplies the type A1 code for modulating the laser. For the demonstrations herein, the PR code $L_c$ was 254 bits long and the clock speed was 100 MHz giving a range resolution $\Delta R = c\Delta t/2 = 1.5$ m, and an unambiguous range (for the A1 code) $L_c(\Delta R/2)=190.5$ m. Noting that the duty factor of the PR modulated laser diode is about 50%, the transmitted power was ~4 mW, for the 9 mW diode employed for this demonstration of the lidar system of the present invention. Work by the present inventors has found that aerosol clouds beyond 190 m can be detected by the lidar system of the present invention. The range was increased to 381 m for recent demonstrations, and aerosol clouds were detected beyond 300 m. FIG. 2 depicts lidar profiles, i.e., aerosol backscatter signal vs. range profiles, obtained in the present invention by cross correlating the received signal with a pseudo-random modulation code applied to the broadcast signals.

A two mirror optical scheme was employed for the laser beam transmitter in a preferred embodiment of the present invention. This arrangement allowed boresighting of the lidar, which was done by adjusting the overlap between the transmitted beam and the telescope field of view (FOV). The range where full overlap of the transmitted beam with the receiver FOV occurred could be varied from about 5 m to 50 m or longer by changing the angle of the transmitted beam. A 150 mm diameter aperture commercial Maksutov-Cassegrain telescope served as the receiver. This telescope was chosen mainly because of its good image quality, good transmittance in the UV and visible wavelengths, and ready availability at a reasonable low cost, despite its size and weight. The telescope in one embodiment of the present invention collects signals from a far field, i.e., from a source remote from the telescope such that signals arriving at the telescope arrive along optical rays nearly parallel (as from a source at infinity). Signals collected by the telescope were divided into three spectral channels by dichroic beam dividers ($BD_1 \ldots BD_3$)—one in UV for detecting the elastic scattered light and two in the visible (blue and green channels) for detecting the fluorescence. Since the lidar system of the present invention can be expected to operate at night, all three channels can be equipped with wide bandpass filters ($F_1 \ldots F_3$). For the UV channel centered at $\lambda_U=375$ nm, the bandwidth used in the present demonstration was $\Delta\lambda_U=\pm5$ nm to accommodate slight changes in laser diode output wavelength, for the blue channel centered at $\lambda_B=440$ n, $\Delta\lambda_B=\pm40$ mm, and for the green channel $\lambda_B=550$ nm, $\Delta\lambda_B=\pm40$ nm. FIG. 1 shows schematically the optical system including lenses for imaging the telescope aperture on the detectors. Optical ray trace analysis was utilized to set the optical configuration, as shown in FIG. 1, to arrange the three detector channels so as to receive signals from signals the same spatial region. The optical ray trace analysis provided an estimate of the overlap function as a function of range for the lidar for any given alignment of the transmitter beam with respect to the FOV of the telescope.

Optical signal detection in the present invention can be done in all the three receiver channels with for example photon counting channel photomultiplier tube modules. The detector outputs from these modules includes TTL pulses corresponding to the photon counts. A multi-channel scaler (MCS) can be used to time resolve and store the data. Excellent time resolution (400 ps) can be achieved by employing a PC based high speed time of flight card. This card may also have multi channel scaling ability. In the bread-board sensor embodiment described here, two such boards can be used with the UV elastic channel detector attached to one time of flight card, whereas the blue and green fluorescence channel detector outputs were multiplexed, so that they could share the second time of flight card. Multiple cards can be used.

During lidar operation of the present invention, the PR coded light from the laser diode was continuously transmitted with continuous code repetitions. Each time a PR code was transmitted, data acquisition was synchronized with the PR code, and the data from every subsequent code length was accumulated with those from earlier codes. Illustratively, each code took 2.54 µs to generate and about $3\times10^5$ data acquisitions/sec were possible, after taking into account the short set up times of the MCS board for every data acquisition. The signal to noise ratio (SNR) of the measured photon signal can be improved substantially by averaging the data, because the SNR improves roughly proportional to $(N)^{0.5}$ where N is the number of signals averaged. For example with $N=3\times10^5$ acquisitions made in a one second measurement, the improvement in SNR was ~561.

Figure 3:
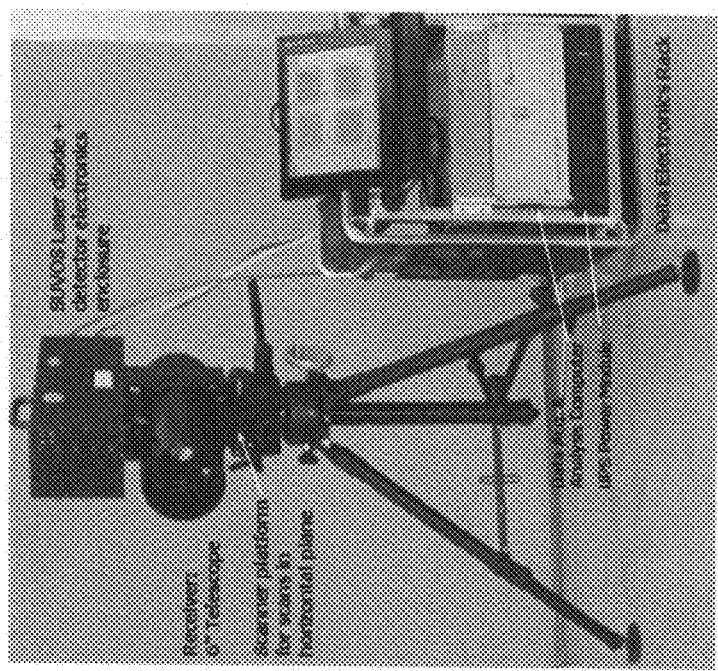
FIG. 3 is a photograph of a portable semiconductor UV laser diode based aerosol and fluorescence lidar breadboard of a preferred embodiment of the present invention.

FIG. 3 shows a photograph of the lidar sensor breadboard. The rectangular enclosure attached to the top of the telescope contains the laser diode transmitter, PRM code generator, laser diode driver, receiver optics train and detectors. A transportable half-height instrument rack (see photograph) contains a rack mount PC used for lidar operation, data acquisition and display. The two time of flight/MCS data acquisition cards were inside the LIDAR computer. Also seen in the top shelf of the rack are the computer display monitor screen and the keyboard. The next component seen in the rack is a box containing dc power supplies for the transceiver head. The component at the bottom of the rack is the UPS power supply. The lidar transceiver head can be mounted on a motorized rotary platform, which in turn is attached to a tripod that provided pan, tilt, and height adjustments for the lidar. The instrument can be leveled such that it scans in a horizontal plane. The rotary table can be programmed to constantly scan over a $\pm13°$ arc, taking approximately 2 minutes for each forward or backward scan.

In one embodiment of the present invention, a software suite assists in lidar operation and data analysis. As described earlier, deriving the target response (i.e., lidar aerosol and fluorescence profiles) from the data obtained with the PRM lidar includes calculating the cross correlation of the averaged PRM signal with the PR code, such calculations being performed in the LIDAR computer or other computer processor. The cross correlation in one embodiment of the present invention can be performed in software. Alternatively, hardware devices can likewise perform the cross correlations. Indeed, correlations involve several computational steps and formerly took very long times before high speed computers were available. Many instruments used hardware correlators which were very expensive. But, use of an efficient mathematical procedure to rapidly complete correlation calculations and the use of a high speed computer permit correlation results to be available in near real-time.

Since the time of flight time resolution is 400 ps, the cross correlation step size $\Delta t=0.4$ ns (the range accuracy $\delta R=6$ cm). A computer program combined with the data analysis algorithm directly provides the target response. The computer program allows real-time operation of lidar by 1) running the lidar system, 2) carrying out data acquisition, 3) doing correlations and 4) displaying the correlation function—which is the target response, or in this case the aerosol cloud and any other hard targets in lidar FOV.

Lidar operation in one embodiment of the present invention sends a series of PRM coded pulses and acquisition of data from the elastic and one of the fluorescence channels for about 6 secs, transfers the MCS outputs to hard disk for storage, and then initiates the next measurement from the elastic and the second fluorescence channel for 6 secs. Each 6 sec measurement corresponded to averaging over an approximately 2° arc, controlled in one embodiment by the above noted computer program.

Large Aerosol Chamber Tests

A lidar system according to one embodiment of the present invention was tested with BW stimulant aerosols in a 70 m$^3$ testing chamber equipped with aerosol dispersal equipment, observation ports, mixing fans, evacuation pumps and HEPA filters. Although the chamber was furnished with optical windows, two windowless shuttered ports were used, the shutter ports being opened for brief periods during the experiments thus avoiding strong elastic scatter and spurious fluorescence from the windows. Such an approach introduced a new constraint in the form of a short observation period (~10 sec), and introduced minor uncertainties in the reported concentrations caused by the opening and closing of ports.

The lidar system according to one embodiment of the present invention was mounted for this test outside the testing chamber on a tripod at a height of 1.5 m above the floor and pointed horizontally through the 200 mm diam. observation port on the chamber wall. The testing chamber had a second, identical port in line with the first on the opposite chamber wall. In this embodiment, the lidar sensor head was aligned during this test so that both the laser beam and the telescope field-of-view passed through the two ports when the inner and outer metal shutters were opened. The lidar sensor head of the present invention was located 5 m from the entrance port, and a beam-stop including a vertically mounted, low-pile black velvet cloth was located 1.5 m beyond the exit port. Aerosol testing path length in the chamber was ~5 m between the entrance and exit ports. A calibrated APS (aerodynamic particle sizer instrument) was located in the center of the chamber below the beam path to provide a continuous record of the estimate of aerosol particle size distributions. The APS data system computed averaged particle size distribution every 20 sec.

A 375 nm CREE™ laser diode with about a 2.6 mW transmitted output power was used. Co-boresight alignment between the laser transmitter and the receiver telescope field-of-view was adjusted for maximum elastic backscatter from the chamber atmosphere. The maximum elastic backscatter in the UBTL lidar was achieved when the laser beam was aligned to cross through the telescope FOV in the chamber and the FOV was increased to its maximum value of 8 mrad. With this configuration, ~$10^5$ counts/sec (cps) was obtained with a 3 m-wide peak in the UV elastic channel from the background atmosphere in the center of the chamber at a range of ~7 m from the instrument. During these background data runs, the chamber atmosphere was composed of ~1000 particles/liter (ppl) of 1 μm mean particle size.

Figure 5:
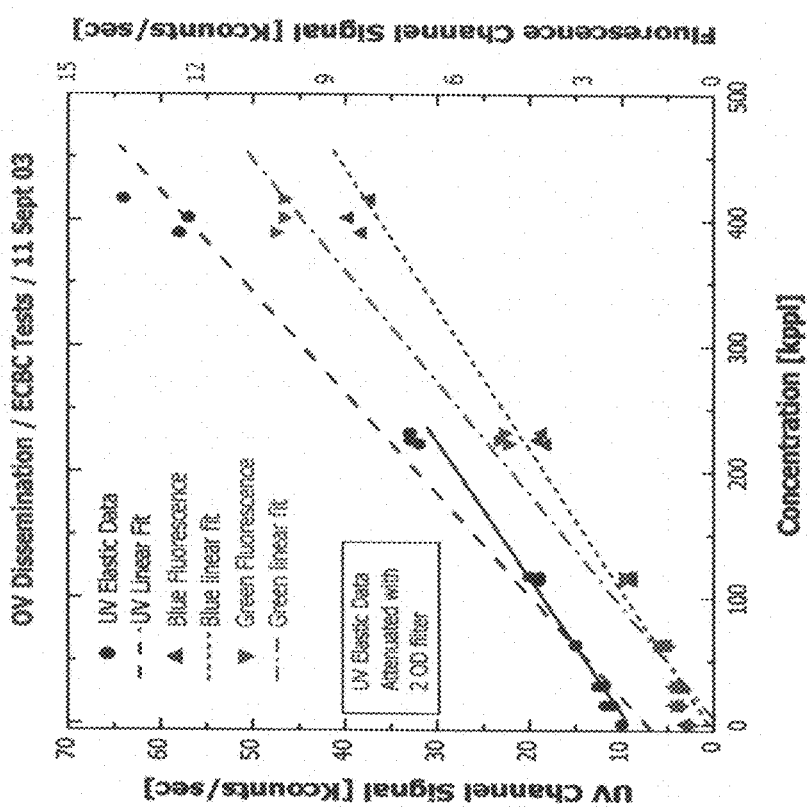
FIG. 5 depicts a signal in the three receiver channels vs. OV (ovalbumin) concentration, as measured against APS.

The UBTL instrument of the present invention was tested with varying amounts of aerosol loadings of stimulants—BG (bacillus globigii), OV (ovalbumin) and Kaolin, and obtained strong blue and green fluorescence signals of several thousand cps, as well as strong elastic backscatter signals. Saturation of the 375 nm UV detection channel was prevented by a neutral density filter with optical density 2 (OD 2), to provide 100:1 attenuation. For the tests with BG, the initial concentration of stimulant in the chamber was about $1.3 \times 10^6$ ppl. Lidar data counts were ~$9 \times 10^6$ photo-electron counts/sec in UV channel after correcting for the attenuator, $1 \times 10^4$ and $3 \times 10^3$ counts/sec in the blue and green fluorescence channels respectively. The aerosol particle concentration in the chamber was lowered in successive increments by approximately a factor of two for each step. For the first six or seven reductions in concentration, both the UV-elastic and fluorescence detector counts decreased approximately by the same factor (see FIG. 4). When the particle concentration was reduced below $2.5 \times 10^4$ ppl, the aerosol fluorescence signal merged into the interfering background signals due to the chamber beam walls and the beam stop. With OV dissemination, the starting concentration was ~$4 \times 10^5$ ppl, (about a third of BG). Photo-electron counts of ~$6.5 \times 10^6$ counts/sec in UV channel, $9 \times 10^3$ and $10 \times 10^3$ counts/sec in the blue and green fluorescence channels respectively were obtained (see FIG. 5), which are only slightly smaller than those for BG. This was expected because of the higher cross sections for OV when compared to those for BG. With Kaolin the starting concentration was $1.1 \times 10^6$ ppl, the counts were ~$2.4 \times 10^7$ counts/sec in UV channel, $2 \times 10^3$ and $1 \times 10^3$ counts/sec in the blue and green fluorescence channels respectively were obtained. Although Kaolin is non-fluorescent, finite signals in both fluorescence channels were obtained—indicating that there was either a leak of elastically scattered photons into the fluorescence channels, or the possibility of impurities in the sample of Kaolin or the contamination of Kaolin with the fluorescent materials in the disseminator.

Measurements of elastic scattered light leaking into the fluorescence channel showed that this was not significant enough to cause the count rate obtained. From FIGS. 4 and 5, the data points corresponding to initial part of the test (when the highest concentration is present) are higher than the linear fit shown by dashed lines in these figures. Larger particles (5 to 10 μm) in the aerosol may have contributed to a higher signal at the start of test, but the larger particles settle out faster thus leaving only the smaller particles (1 to 3 μm) in the aerosol cloud for the latter part of the test. Larger particles have a much larger backscattering and fluorescence cross section when compared to the 1 to 3 μm particles. This could account for the increased lidar signal at the start of the test.

Field Tests

A lidar system according to one embodiment of the present invention was tested under ambient, field conditions including at nighttime in a 2-km field test grid. Field tests involved dissemination of various bio-warfare stimulants such as BG, EH, and MS2, and interferents during multiple test windows on separate nights. Various dissemination methods including ground point and line sources, ground-based vehicle, and aircraft were used.

The field tests included nighttime blind disseminations of stimulant, or interferent aerosols for short durations (10 to 20 min) during specific time windows. These downwind disseminations were released at an unknown distance upstream from the instruments so that the wind carried the aerosol clouds over the sensors. Since the wind pattern and the spread of the aerosol could not be determined prior to the test, the UBTL sensor in the lidar system of the present invention was continuously scanned in the horizontal plane for these tests. For these tests, the horizontal scan pattern was set to a nominal 26° full-angle scan at 0.2°/sec angular speed with a continuous back and forth motion, in order to extend the spatial coverage of the UBTL lidar measurements to a wedge-shaped sector region. However, no elevation scans were done during these experiments. The UBTL instrument assembly of the present invention for these tests was mounted in the back of a truck with the lidar FOV pointing within 1° of horizontal, at a height of 2 m above the local ground level. The UBTL FOV was unrestricted except for a hard-target presented by a 2 m high mini-trailer at ~130 m range. The body of the trailer blocked the beam for approximately a 2° sector (where the lidar signals were saturated), and served as a pointing reference to calibrate the scan angle. The scanner did not have an encoder, and only relative scan angle command information was available.

For these demonstrations, 375 nm CREE™ laser diodes were utilized. The diode cw output was ~10 mW so that the transmitted power was ~5 mW. The transmitted beam and telescope FOV were fully overlapped from about 30 m range. With this configuration, the UV elastic backscatter signal from 30 m range in ambient atmosphere was comparable to the signal from 7.5 m range in the large aerosol chamber (discussed above).

For real time analysis of the lidar data, the lidar software described above included programming steps to produce lidar-waveform displays, to provide backscattered elastic and fluorescence signatures as a function of range, and to tabulate the total counts per sec under the correlation lidar curve as well as the total counts under the backscatter peak (integrated down to 5% of the peak value). Data obtained includes a series of detector counts S(N), the number N is the number of time intervals to accommodate one code length on the MCS data system. The data obtained being equal to the time for one full code length×sampling rate (e.g., 2.54 microsec×2000 samples/microsec) as in the UBTL of the present invention with 100 MHz clock, 254 bit code, 500 ps MCS data system. If the PR code used is C(N), then the cross correlation consists of calculating functions such as $\Sigma_N S(N) \cdot C(N+k)$; where k=0, N−1. i.e., this function is calculated N times each time with the code moved ahead by one step. The step size is of course the time step (here 500 ps) with which the signal return is collected. When converted to range, the smallest step corresponds to the accuracy with which the round trip time of light from the lidar to target and back is measured, which is equal to 12 cm or in terms of range accuracy it is the one way distance=6 cm. The total time for one code length corresponds to the longest unambiguous range that can be used—here it is 2.54 μs or 190.5 m range (round trip distance is 381 m). The true range resolution corresponds to one clock period which is 10 ns or $\Delta R = c \cdot \Delta t/2 = 1.5$ m.

For visualization of the aerosol cloud events, quick-look data analysis routines were included in the LIDAR software. In this technique, the raw data in the elastic channel and the fluorescent channels is converted to lidar profiles (i.e., aerosol strength and fluorescence strength) and stored as a function of range. This data is also plotted as false color plots in 1- or 2-D displays. This analysis procedure constructs a false color strip chart display by arranging each of the successive lidar backscatter or fluorescence signal versus range (R) profiles (i.e., correlation function counts rendered in false color vs. range) in a time series plot.

Figure 6:
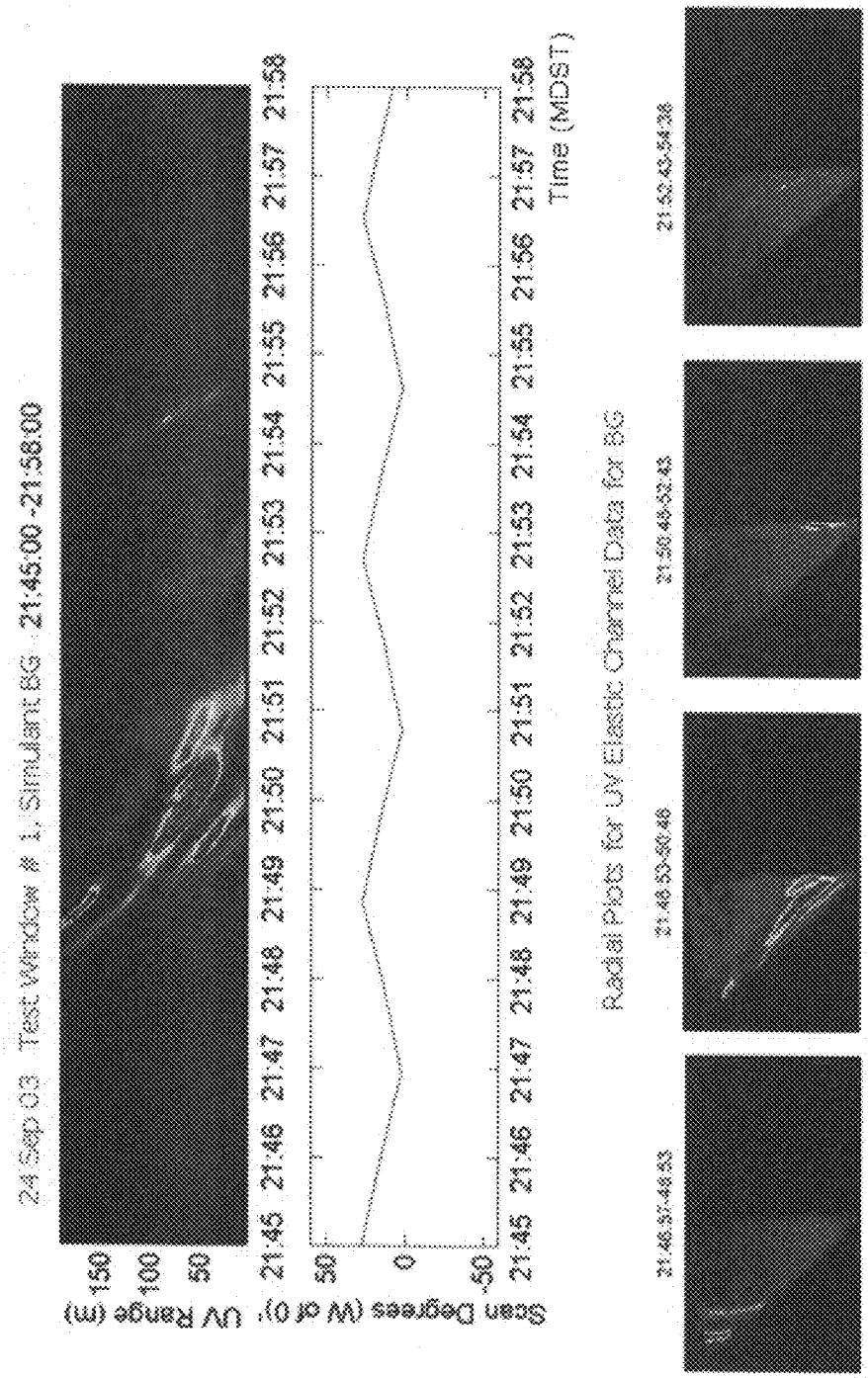
FIG. 6 is a one-dimensional time series color image of aerosol cloud evolution for BG stimulant release.

FIG. 6 shows the UV elastic channel false color time series lidar signal vs. range plots for BG dissemination. In this one-dimensional plot, the x-coordinate is time, which increases monotonously from left to right. The data thus corresponds to scans first in clockwise direction and then in the counterclockwise direction approximately every two minutes. In these plots, dark blue color denotes the baseline signal (or low signal), with the lighter blues, yellows and reds denoting successively higher signal strength. Although this display provides an indication of aerosol cloud evolution, spatial information regarding the scanner azimuth is lost.

Figure 4:
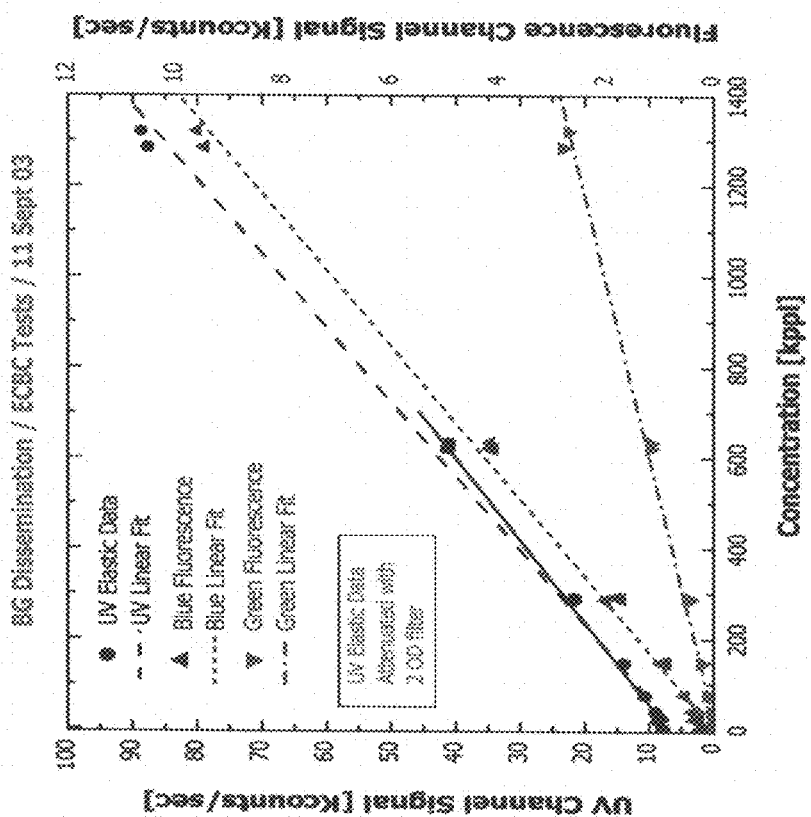
FIG. 4 depicts a signal in the three receiver channels vs. BG (*bacillus globigii*) particle concentration, as measured against an aerodynamic particle sizer (APS)

A more effective way of visualizing the data in its proper spatial orientation is to plot the data in the radial R-θ format. FIG. 4 shows the radial plots of the same UV elastic channel data for 4 scans covering the time period 21:46 to 21:55 hrs. Each of the radial plots represents a 2-dimensional snapshot of the aerosol cloud, and successive plots show the evolution of the aerosol cloud.

Figure 7:
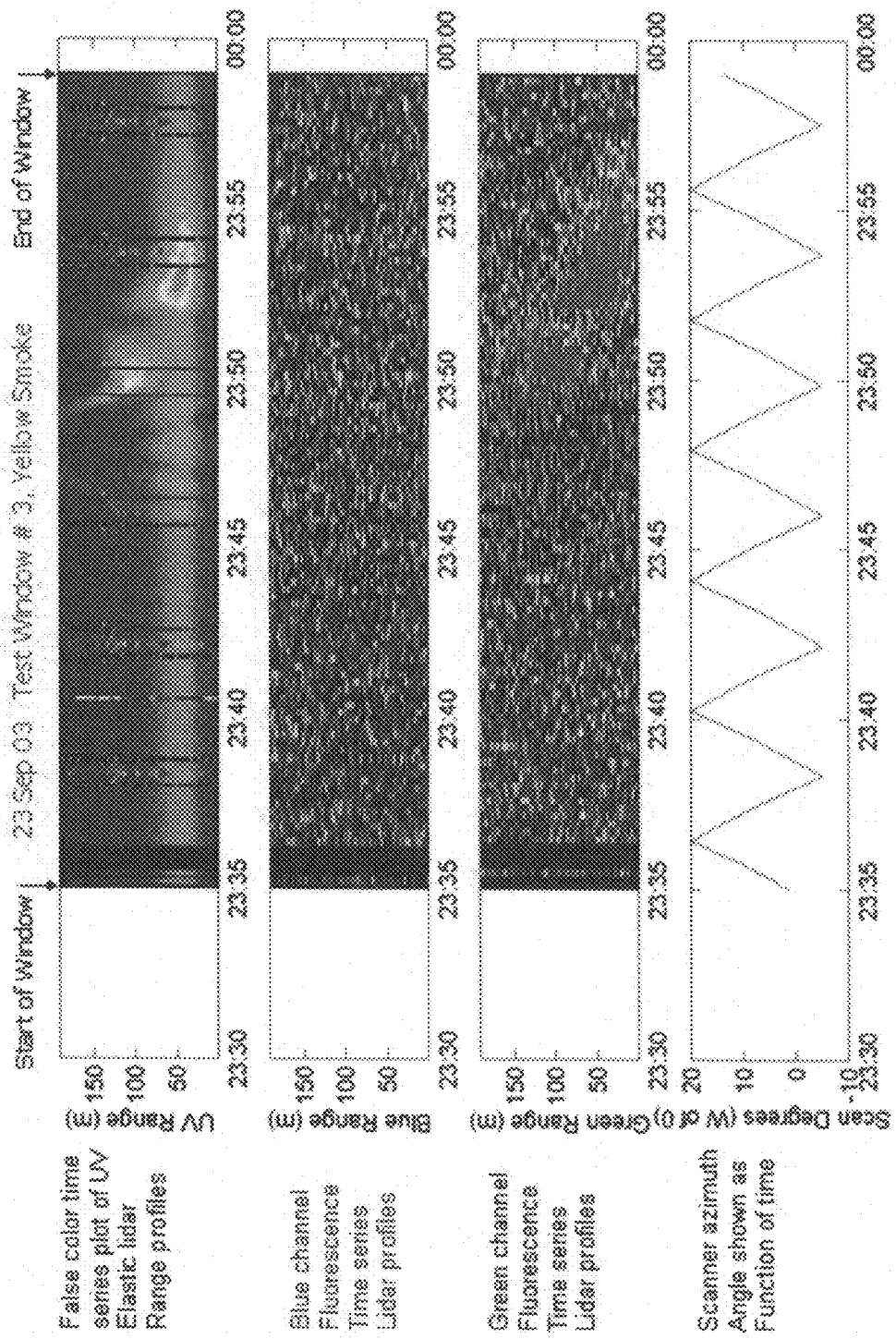
FIG. 7 is a false color time series depiction of lidar range profile data shown for yellow smoke grenade (interferent) release.
Figure 8:
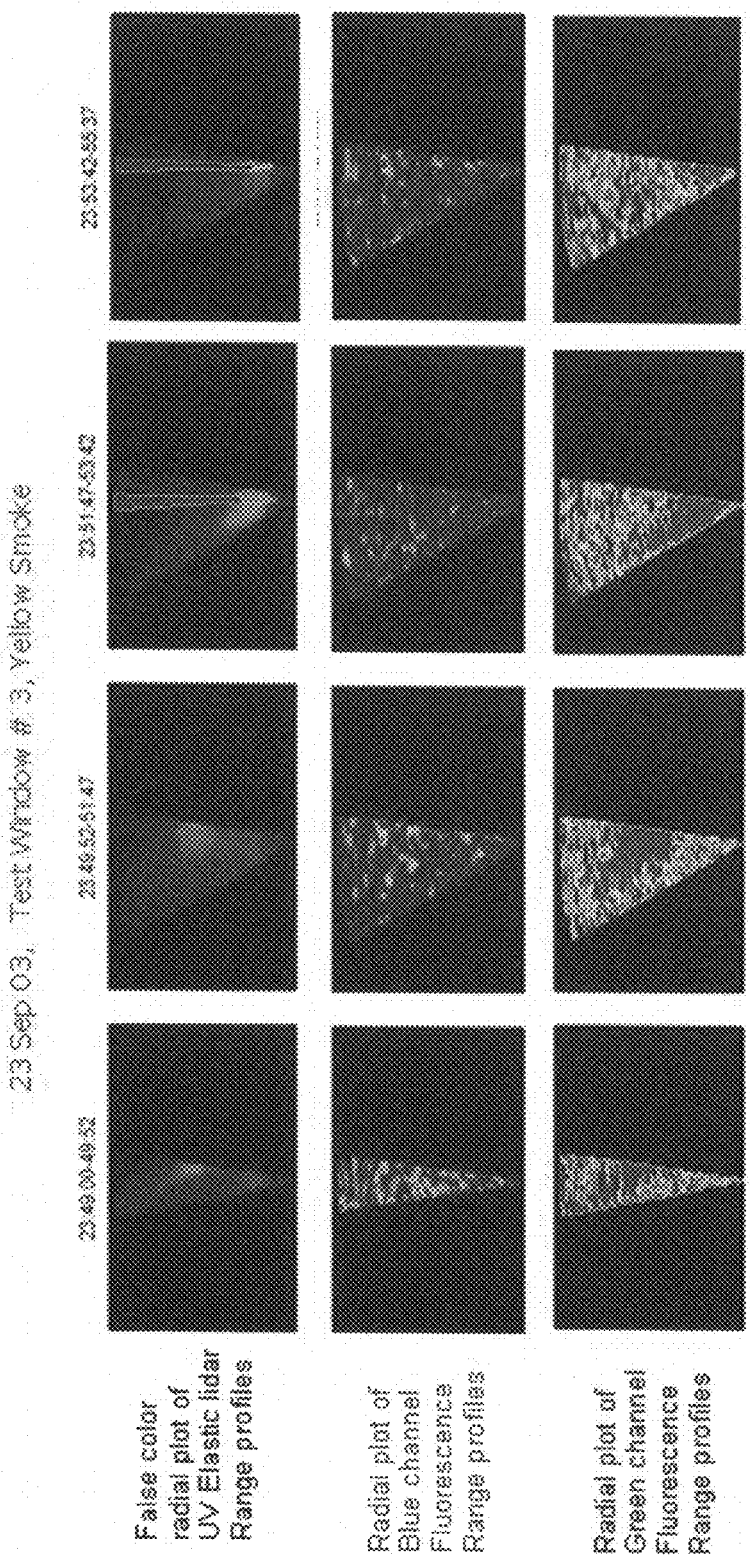
FIG. 8 is a two-dimensional (R-θ) false color aerosol cloud images for the time series depicted in FIG. 7.

FIG. 7 shows the false color time series lidar signal vs. range plots for all three channels, i.e., UV elastic, blue and green fluorescence for yellow smoke (interferent) dissemination. Data from each of the three spectral channels are shown in separate data windows. The vertical stripes in the UV elastic channel (top window) correspond to the trailer blocking the lidar FOV. Here also, blue color denotes the baseline (or low signal), with the yellows and reds denoting higher signal strength. FIG. 8 shows the radial plots of the same data in the three spectral channels for 4 scans covering the time period 22:49 to 22:56 hrs.

From FIGS. 7 and 8, the events occurring in the observation window are interpreted. Starting a little after 22:46 an enhanced signal was observed in the UV elastic channel and extended to beyond 22:56. This is assumed to be due to the aerosol cloud release. It is noted that there was a strong signal in the green fluorescence channel whereas there is no such clear signal in the blue fluorescence channel. Also noted is the increased background (range independent) signal between 22:42 and 22:49 in both the blue and green fluorescence channels. The increased background is likely due to strong illumination in the telescope FOV from a secondary source not intentionally introduced.

Figure 9:
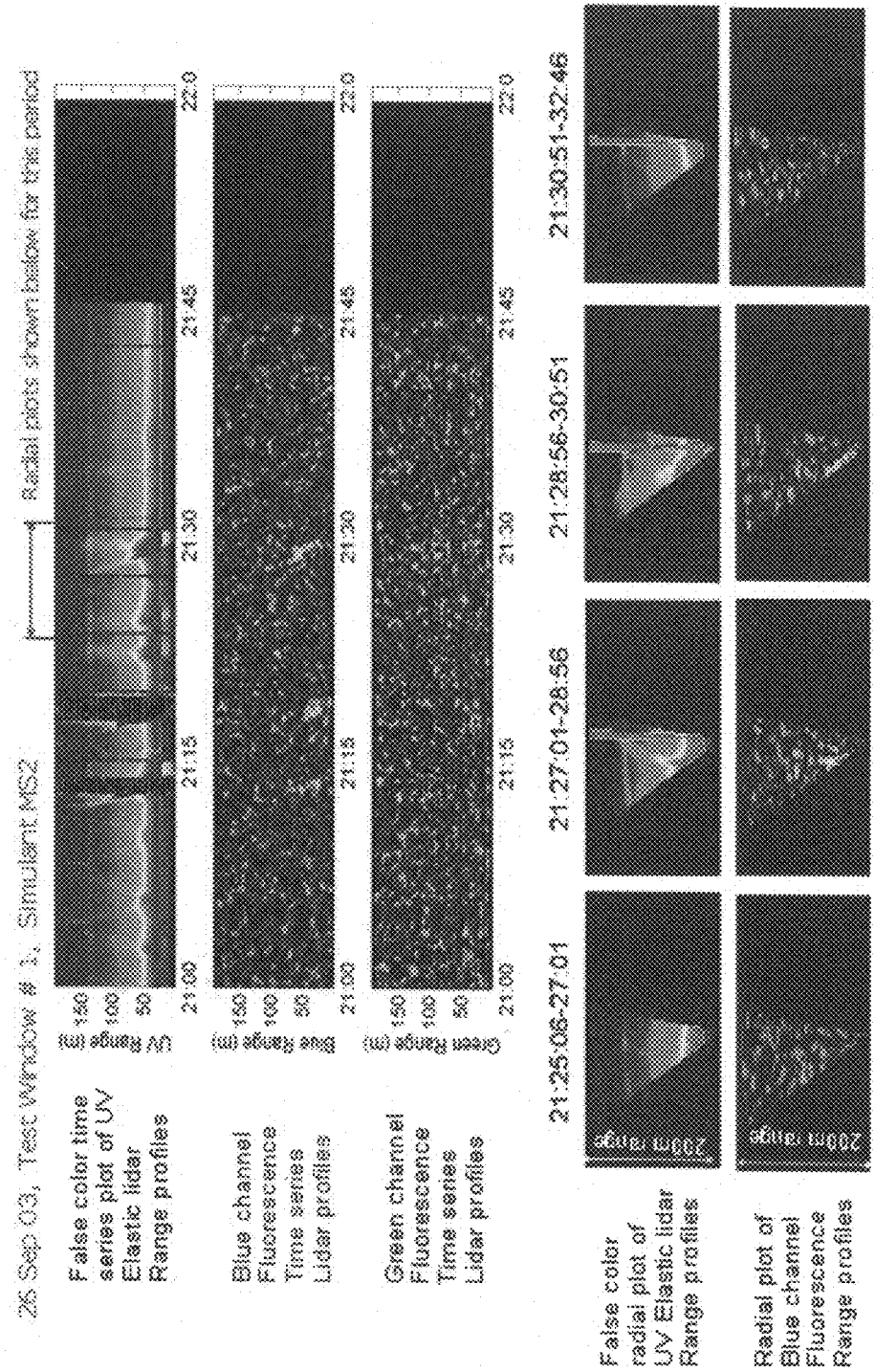
FIG. 9 is a false color 1-D time series depiction and two-dimensional lidar range profile data shown for stimulant (MS2) release.

FIG. 9 shows the false color time series and the radial plots for another test window, where a stimulant MS2 was disseminated. UV elastic channel data indicates start of disseminant release at ~21:12 and continuing up to 21:32, with a break in the middle. Strong fluorescence is seen in the blue fluorescence channel but not in the green channel.

The UBTL sensor of the lidar system of the present invention using a 375 nm SUVOS laser diode with 5 mW transmitted power has demonstrated stand-off measurements of BW agent stimulant aerosols and interferents with a few hundred meter range. The UBTL sensor of the present invention has demonstrated that fluorescence measurements at up to 100 m range. By combining the PRM lidar technique with photon counting detection, a compact UBTL sensor has established that, even with as little as 5 mW of laser power, a practical stand-off sensor is realized. Cloud extent, and cloud tracking have also been shown to work effectively by using an azimuth scanner. The instrument sensitivity for BG fluorescence was roughly estimated to be ~10 Kppl, whereas aerosol elastic scatter detection levels were ~1 Kppl. This estimate is based on the lidar response measured during the ECBC test with BG. By optimization of the optics and by increasing the laser power we expect to reach fluorescence detection sensitivity levels approaching 1 Kppl. The present invention can be further complemented with an algorithm for the real time discrimination of BW aerosols from other types of aerosols and complemented with additional excitation and detector channels.

One function of the bio-lidar is to effectively discriminate between BWA clouds and other non-hazardous clouds or interferents, so as to achieve reasonable false alarms incidence rates of <1 in every 24 hours. Whereas aerosol cloud detection relies on information from the elastic channel, discrimination requires the signals from Fluorescence channels. Together, these three signal returns define an aerosol cloud signature to compare against a database to classify the type of cloud. While the lidar system of the present invention cannot identify the exact material make-up of an aerosol cloud, it is able to discriminate between Agents of Biological Origin (ABO) and obscurants, naturally occurring pollens, and petrochemical fumes.

The optical fluorescence sensors in the present invention are suitable as both trigger and detect-to-warn devices because of their rapid response and negligible operating costs. Auto-fluorescence is generated when the BWA particles are excited with UV or visible radiation. The main fluoro-phores are: 1) Aromatic amino acids tryptophan, tyrosine, and phenylalanine: excitation—240-280 nm and fluorescence—280-350 nm; 2) NADH and NADPH: excitation peak—340 nm and fluorescence peak—450 nm; and 3)

Flavin compounds: excitation peak—450 nm and fluorescence 515-565 nm. Discrimination between biological and non-biological particles can for example be achieved in the present invention by comparing the fluorescence intensities at these wavelengths. The size and shape morphology of BW agent particles can also used in addition in some of these sensors to improve the discrimination. This requires measurement of elastic scatter in addition to fluorescence.

The BWA sensor of the lidar system of the present invention can effectively discriminate between the fluorescence from BWA particles and other naturally occurring non-bio (dust, smoke and soot, etc) and bio-particles (such as, pollen, human and animal cells, other background bacteria and fungal spores), and interferents, with very low probability for false alarms $P_{fa}$. Several measurable parameters have been considered for discrimination, and include fluorescence intensities in one or more spectral bands corresponding for example to tryptophan (340 nm), NADH (440 nm) or Flavin (540 nm), and elastic scattering in one or two wavelengths for inferring the size of particles.

The lidar system of the present invention performs an analysis of the aerosol cloud that can accurately discriminate between ABO's and non-threatening aerosols in ten seconds. Fluorescence aerosol particle sensors of the present invention utilize a procedure similar to that demonstrated by the BAWS sensors as described by Jeys, 1998, Primmerman, 2000, the entire contents of which are herein incorporated by reference, where the relative fluorescence efficiencies are calculated in the two spectral regions and normalized to the elastic signal.

Figure 10:
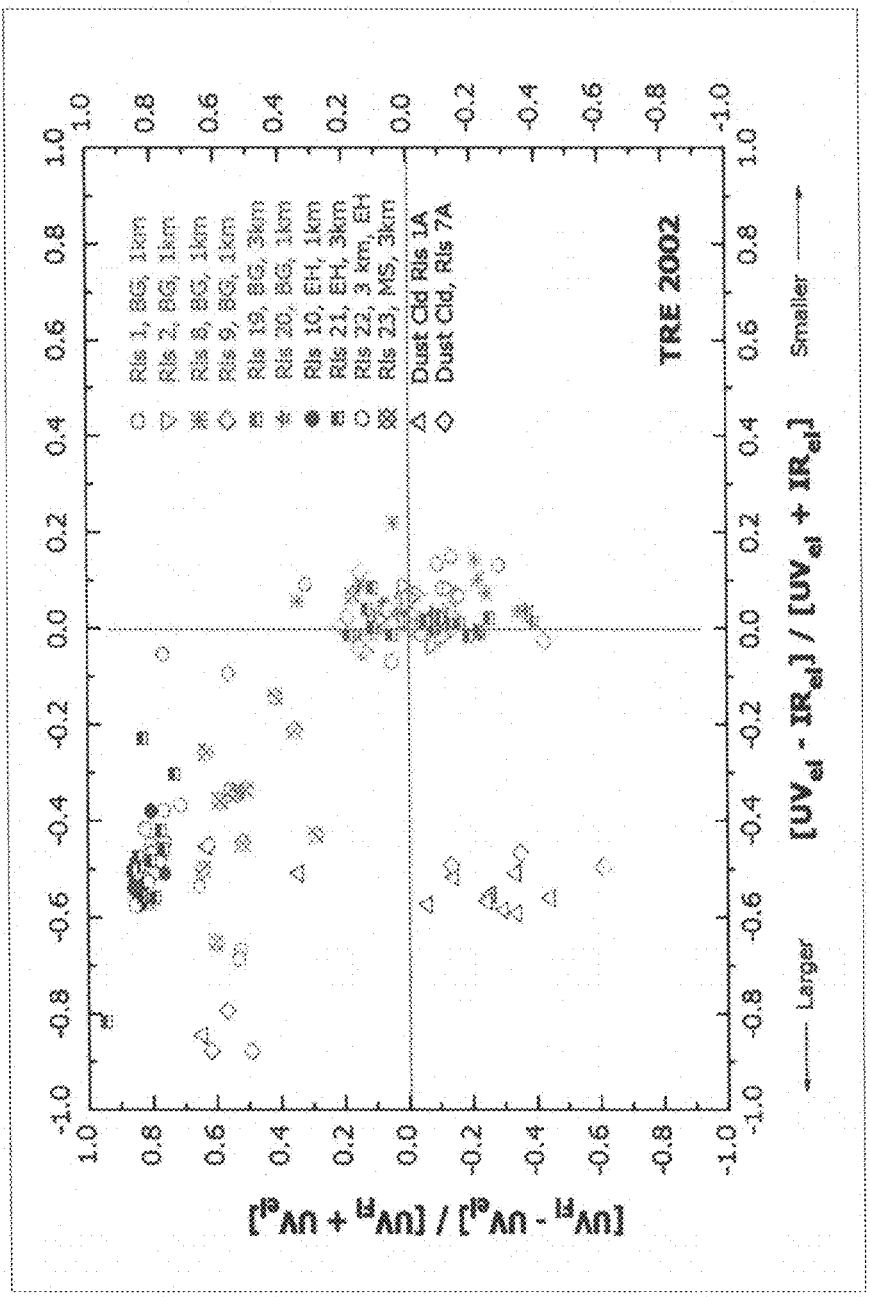
FIG. 10 depicts a two parameter plot of several BWA stimulants and interferents detected by the lidar system according to a preferred embodiment of the present invention.

The detection/analysis technique of the present invention includes in one embodiment an additional elastic scatter channel in the IR (e.g., 1 μm). By comparing the IR elastic and UV elastic channels, the stand-off lidar sensor can determine X, a particle size parameter. By comparing the FL and UV elastic channels, the stand-off lidar determines Y, a particle fluorescence efficiency parameter. In this two-parameter space, many of the known threat agents tend to aggregate in a fairly small region so that it is possible to segregate the threat agents from all other types of aerosols with a high probability. FIG. 10 shows the two parameter plot of several BWA stimulants and interferents tested by the stand-off lidar according to one embodiment of the present invention. Signal in each channel is multiplied by empirically determined weighting factors (a, b, and c) in order to place the bacterial spore stimulant BG signature at the center of the plot. BG is accepted as the standard for testing lidars, since is readily available, non-hazardous and is more difficult to detect and discriminate than other stimulants. As FIG. 10 demonstrates, aerosol signatures group together allowing for ease of classification.

The boundaries of each of the species groupings are then defined in the database against which all aerosol signatures are compared.

Discrimination Algorithm

By adopting this process of determining particle size and fluorescence, the computer algorithm has the ability to quickly process data and discriminate on objects of interest. As discussed in the previous section detailing object detection, each channel has a consistent background level. This background must be appropriately subtracted in order to determine the signal returning from objects of interest. The process for determining and subtracting these background levels were described in detail in the previous section.

After the signal for the object of interest is found in each channel, the signals must be properly correlated and compared. It is possible that the signals in the three channels may be displaced in range by one or more range bins. Depending on the nature of the object of interest, some wavelengths might penetrate deeper into the cloud than others. Hence, the signals are correlated in range first so that the signals will all be measured at the same distance. Secondly, the size of the cloud is set by the smallest elastic signal. That is, if the UV channel determines that the cloud is 45 m deep and the IR sees 63 m into the cloud, only the first 45 m of the cloud are analyzed. The signal from each channel is then defined as the total signal in the range of interest.

The signature as defined previously has a range dependence due to atmospheric effects and system optical parameters. To simplify the discrimination process in one embodiment of the present invention, the range dependence is mathematically determined and the signals corrected. Each wavelength of light has a different extinction coefficient that is dependent on atmospheric quality. Each channel also has a different overlap function, that is, the percentage of signal collected vs. range is different for each channel. The possibility of the laser energy changing over time is also accounted for in this embodiment. And finally, it is the nature of photon-counting modules to have a non-linear response when the signal gets too strong (dead-time correction). The non-linear response of each detector, as determined by the manufacturer, is verified, and programmed into the discrimination algorithm by the following procedure:

$s_J(R)$=Raw signal in detection channel J
$E_J$=Transmitted laser energy in channel J
$\Phi_J(R)$=Overlap function for channel J
$T_J(R)$=Atmospheric transmittance for channel J=$\exp[-2\alpha_J(R)]$
$\alpha_J(R)$=Extinction coefficient
J=IR=Near IR elastic channel
=UV=UV elastic channel
=F=Fluorescence inelastic channel
$s_{IR}(R)$=IR channel Elastic Scatter Signal
$s_{UV}(R)$=V channel Elastic Scatter Signal
$s_F(R)$=Florescence Channel Signal (UV Laser induced)

Normalized signal calculation $S_J(R)$:

$$S_J(R) = \frac{s_J(R) \cdot \zeta_J(s_J)}{E_J \cdot \Phi_J(R) \cdot T_J(R)}$$

1. Dead time correction $\zeta_J(s_J)$
2. Energy Normalization $E_J$
3. Overlap Correction $\Phi_J(R)=A_0+A_1R+A_2R^2+A_3R^3+A_4R^4$
4. Extinction correction=$T_J(R)$ Averaged Signal:

$$\overline{S_J} = \sum_{10\ sec} S_J(R)$$

Discrimination Parameters:

$$X = \frac{a\overline{S_{IR}} - c\overline{S_{UV}}}{a\overline{S_{IR}} + c\overline{S_{UV}}};\ Y = \frac{b\overline{S_F} - c\overline{S_{UV}}}{b\overline{S_F} + c\overline{S_{UV}}}$$

where a, b and c are discrimination constants required for BG classification to be placed in the middle of the X-Y plot.

Fluorescence Lifetime Measurements

Although fluorescence sensors work reasonably well for discriminating BW agents, it is well established that certain types of naturally present aerosols (dust, pollen, soot, etc) and interferents (smoke, polycyclic aromatic hydrocarbons, etc) can cause the sensors to produce false alarms. Based on information regarding the types of aerosol particles encountered, the present invention, while not restricted to the following, draws some general conclusions:

1) Soil derived particles do not cause significant problems;
2) Among the naturally occurring biological particles such as fungal spores, natural bacteria and pollen, the fungal spores are the most likely to cause false alarm because of their similarity to the BWA and higher concentrations. Natural bacteria and pollens do not pose serious problems because their concentrations are low. Further natural bacteria and pollens can be discriminated on the basis of size as the bacteria are normally attached to larger particles or as in the case of pollen are much larger (e.g. 20-100 µm);
3) The particulates that cause considerable difficulties for discrimination are polycyclic aromatic hydrocarbons (PAH)—products of incomplete combustion of diesel and other fuels. Not only are these strongly fluorescent but can also mimic the BW agent signature and size when they are adsorbed on other particles leading to false alarms.

One approach for improving the performance of the fluorescence sensor is to add more discrimination parameters, such as fluorescence in several additional or narrower spectral channels, particle shape dependent parameters such as depolarization, to improve discrimination, and thus reduce the combined probability for false alarm. Although with the addition of more fluorescence and elastic spectral channels the probability $P_{fa}$ is expected to reduce to below $10^{-3}$ level, further reduction of $P_{fa}$ to the required $2\times10^{-4}$ level is unlikely from only this approach. This is because these additional parameters are not truly independent and hence do not provide uncorrelated measurements. Accordingly, the present invention in one embodiment utilizes the fluorescence lifetime $\tau_f$, for discrimination between BW agents and other interferents. The fluorescent lifetimes of many of the interferents are sufficiently different from that for the BW agents so as to provide a robust discriminant. For example, the lifetimes $\tau_f$ of many aromatic hydrocarbons such as Benzene, Xylene, Toluene, Naphthalene, Phenylcyclohexane, are in excess of 100 ns, whereas most of the bacterial and other BW agent lifetimes are in ~2 to 6 ns range.

The excellent time resolution capabilities (~100 ps) of the PRM technique employed in certain embodiments of the present invention permit PRM to simultaneously measure fluorescent lifetimes of the aerosol particles as well. With a time resolution of a 100 ps, it is expected that the BW agents whose lifetimes range from 2-5 ns, can be differentiated effectively against the common interferents mentioned above. The discrimination algorithm can be expanded to include fluorescence lifetime as an additional discrimination parameter.

Computer Acquisition and Processing

Figure 11:
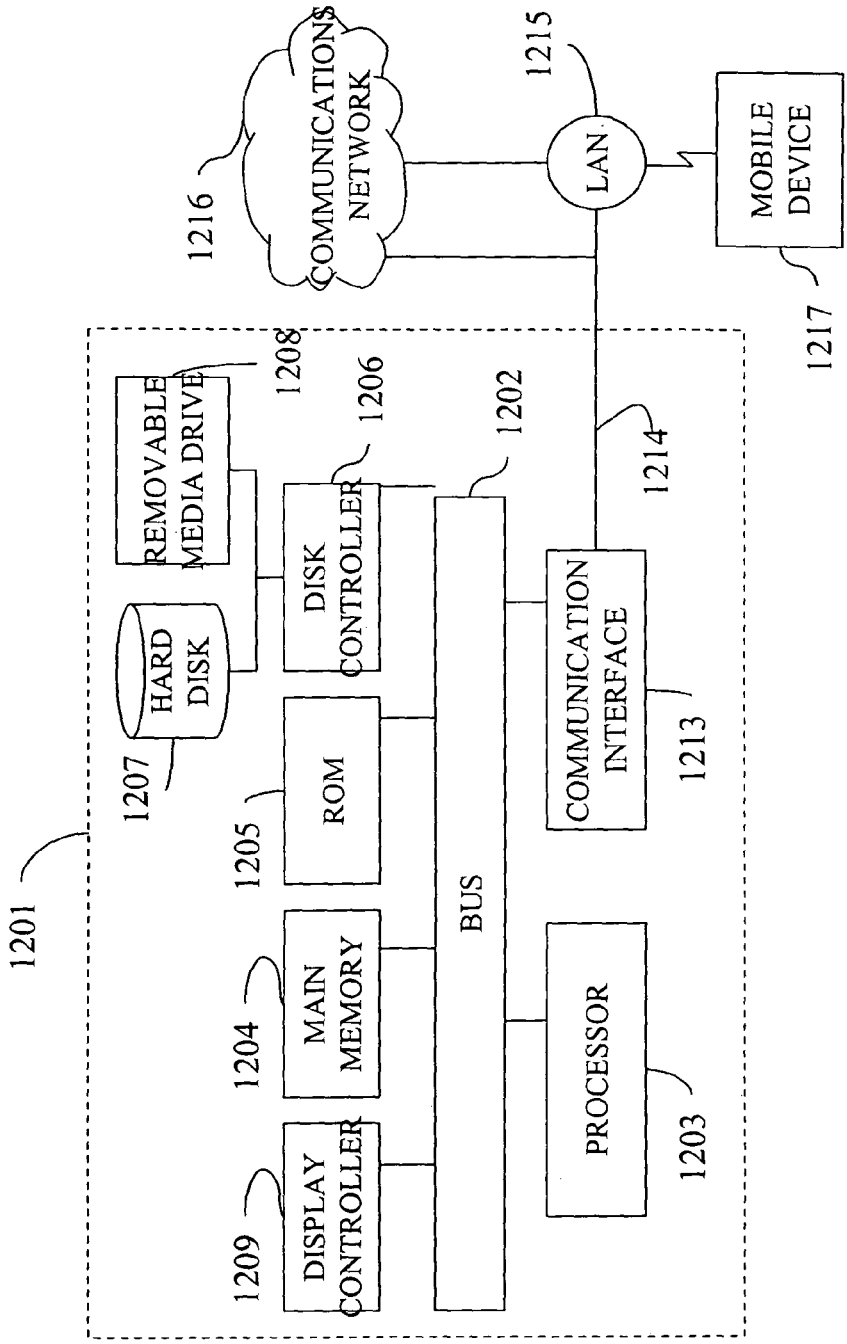
FIG. 11 illustrates one embodiment of a computer system utilized by a lidar system of the present invention that may be implemented.

FIG. 11 illustrates one embodiment of a computer system 1201 in which a lidar system according to one embodiment of the present invention can be implemented. The computer system 1201 is programmed and/or configured to perform any or all of the functions of the control circuit for laser operation, the PR code generator, and/or the LIDAR computer described above. The computer system 1201 includes a bus 1202 or other communication mechanism for communicating information, and a internal processor 1203 coupled with the bus 1202 for processing the information. The computer system 1201 includes a memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by the internal processor 1203. In addition, the memory 1204 may be used for storing temporary variables or other intermediate information during the execution of instructions by the internal processor 1203. The computer system 1201 preferably includes a non-volatile memory such as for example a read only memory (ROM) 1205 or other static storage device (e.g., programmable ROM (PROM), erasable PROM (EPROM), and electrically erasable PROM (EEPROM)) coupled to the bus 1202 for storing static information and instructions for the internal processor 1203.

The computer system 1201 may include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

Figure 12:
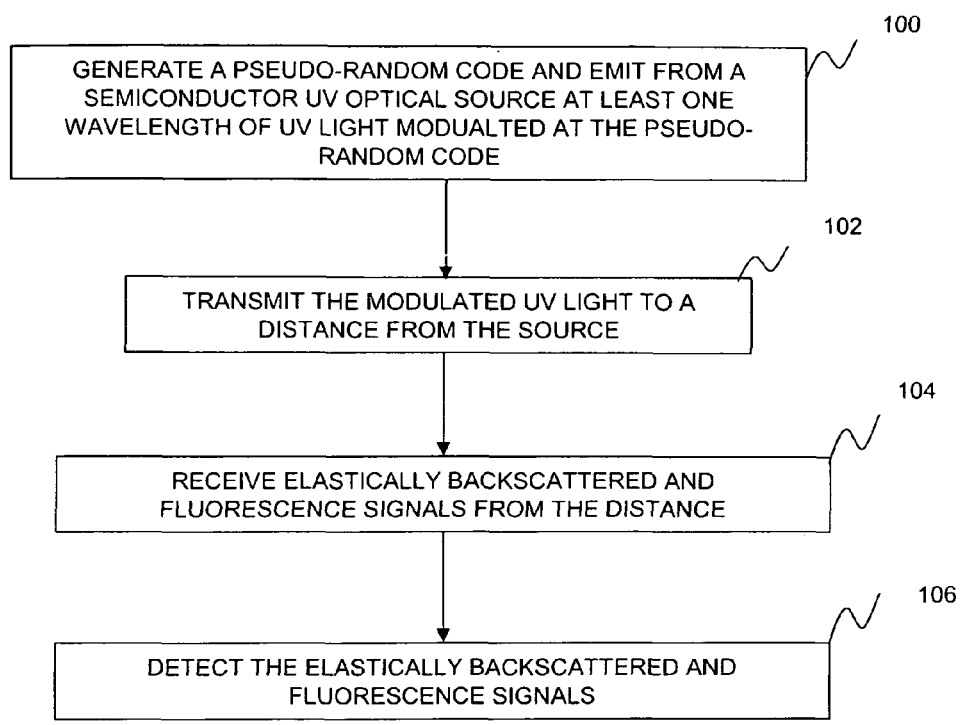
FIG. 12 depicts a flowchart illustrating one preferred method of the present invention.

The computer system 1201 performs a portion or all of the processing steps of the invention in response to the internal processor 1203 executing one or more sequences of one or more instructions contained in a memory, such as the main memory 1204. Indeed, FIG. 12 is a flowchart illustrating one method of the present invention that can be controlled by the computer system 1201 (or alternatively can be performed with individual processors or performed separately from the computer system 1201). As shown in FIG. 12, at step 100, a pseudo-random code is generated and at least one wavelength of ultraviolet light modulated at the pseudo-random code is emitted from a semiconductor ultraviolet optical source. At step 102, the modulated ultraviolet light is transmitted to a distance from the source. At step 104, elastically backscattered and fluorescence signals are received from the distance. At step 106, the elastically backscattered and fluorescence signals are detected.

Such instructions may be read into the main memory 1204 from another computer readable medium, such as a hard disk 1207 or a removable media drive 1208. Such capability being compatible mostly with the embodiment in which the electronic monitoring device is outside the semiconductor processing system 12. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media suitable for the present invention are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., to interact with consumable part disposal personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the internal processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to internal processor 1203 for execution. For example, the instructions may initially be carried on a magnetic disk of a remote computer. The remote computer can load the instructions for implementing all or a portion of the present invention remotely into a dynamic memory and send the instructions to the electronic monitoring device 10. An infrared detector coupled to the bus 1202 can receive the data carried in the infrared signal and place the data on the bus 1202. The bus 1202 carries the data to the main memory 1204, from which the internal processor 1203 retrieves and executes the instructions. The instructions received by the main memory 1204 may optionally be stored on storage device 1207 or 1208 either before or after execution by the internal processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

Numerous modifications and variations of the present invention are possible in light of the above teachings. It is therefore to be understood that within the scope of the appended claims, the invention may be practiced otherwise than as specifically described herein.

The invention claimed is:

1. A system for detecting airborne agents, comprising:
   a semiconductor ultraviolet optical source configured to emit at least one wavelength of ultraviolet light;
   a controller configured to generate a pseudo-random code for emission of the ultraviolet light, said emission of the ultraviolet light being emitted at least one wavelength which is modulated at the pseudo-random code;
   transmission optics configured to transmit the ultraviolet light to a distance from the optical source to the airborne agents;
   reception optics having a receiver which is the first optical component in the reception optics to receive from said distance both 1) elastically backscattered signals indicative of a particle size of the airborne agents and 2) fluorescence signals from the airborne agents, wherein both the receiver and the reception optics are separated from the transmission optics;
   at least two dichroic beam splitters disposed in the reception optics, in optical communication with the receiver, and separated from the transmission optics, and located on a same collinear optical path therebetween which receive both the elastically backscattered signals and the fluorescence signals; and
   the at least two dichroic beam splitters configured to split the backscattered signals and the fluorescence signals toward respective detectors for measurement of the backscattered signals and the fluorescence signals.

2. The system of claim 1, further comprising:
   a processor configured for a range determination for the airborne agents.

3. The system of claim 2, wherein the processor is configured to determine a chemical identity of the airborne agents from the detected fluorescence signals.

4. The system of claim 3, wherein the processor is configured to analyze a simultaneous measurement of fluorescence lifetimes at different fluorescence emissions.

5. The system of claim 3, wherein the processor is configured to discriminate between bio-warfare agents and non pathogenic aerosols.

6. The system of claim 1, further comprising:
an infrared light source configured to emit at least one wavelength of infrared light from the system.

7. The system of claim 6, wherein the infrared light source is configured to be modulated by at least one of the pseudo-random code and another pseudo-random code.

8. The system of claim 6, further comprising:
a processor configured to determine a particle size of the airborne agents by comparison of a backscattered signal of the infrared light to the backscattered signal of the ultraviolet light.

9. A method for detecting airborne agents, comprising:
generating a first pseudo-random code and emitting from a semiconductor ultraviolet optical source at least one wavelength of ultraviolet light modulated at the first pseudo-random code;
transmitting with transmission optics the modulated ultraviolet light to a distance from the source to the airborne agents;
receiving, with reception optics having a receiver which is the first optical component in the reception optics to receive from the distance both 1) elastically backscattered signals indicative of a particle size of the airborne agents and 2) fluorescence signals, wherein both the receiver and the reception optics are separated from the transmission optics and both the elastically backscattered signals and the fluorescence signals being received along a same collinear optical path between at least two dichroic beam splitters disposed in the reception optics, in optical communication with the receiver, and separated from the transmission optics, where the dichroic beam splitters split the backscattered signals and the fluorescence signals into separate spectral regions for measurement of the backscattered signals and the fluorescence signals;
detecting the elastically backscattered and fluorescence signals; and
determining and outputting an identity of the airborne agents.

10. The method of claim 9, further comprising:
analyzing the detected signals for a range determination of the airborne agents.

11. The method of claim 9, further comprising:
analyzing the detected signals for a chemical identity of the airborne agents.

12. The method of claim 11, further comprising:
measuring fluorescence lifetimes at different fluorescence emissions.

13. The method of claim 11, further comprising:
discriminating between bio-warfare agents and non pathogenic aerosols.

14. The method of claim 9, further comprising:
generating a second pseudo-random code for modulating an emission of at least one infrared wavelength from an infrared light source; and
transmitting at the second pseudo-random code modulated infrared light from the infrared light source.

15. The method of claim 14, further comprising:
determining a particle size of the airborne agents by comparison of a backscattered signal from the infrared light to the backscattered ultraviolet light signal.

16. A non-transitory computer readable medium containing program instructions for execution on a computer system, which when executed by the computer system, cause the computer system to perform the steps of:
generating a first pseudo-random code for modulating ultraviolet light at the first pseudo-random code;
controlling a semiconductor ultraviolet optical source for emission of at least one wavelength of ultraviolet light which is modulated at the pseudo-random code, said at least one wavelength of ultraviolet light being transmitted with transmission optics;
detecting, with reception optics having a receiver which is the first optical component in the reception optics to receive from a distance of the airborne agents from the ultraviolet optical source both 1) elastically backscattered modulated ultraviolet light signals indicative of a particle size of airborne agents and 2) fluorescence signals from the airborne agents, wherein both the receiver and the reception optics are separated from the transmission optics and both the elastically backscattered signals and the fluorescence signals being received along a same collinear optical path between at least two dichroic beam splitters disposed in the reception optics, in optical communication with the receiver, and separated from the transmission optics, where the dichroic beam splitters split the backscattered signals and the fluorescence signals into separate spectral regions for measurement of the backscattered signals and the fluorescence signals;
analyzing the detected signals for an identification of airborne agents; and
determining and outputting an identity of the airborne agents.

17. The computer readable medium of claim 16, wherein the program instructions cause the computer system to perform the step of:
analyzing the detected signals for chemical analysis of the airborne agents.

18. The computer readable medium of claim 17, wherein the program instructions cause the computer system to perform the step of:
measuring fluorescence lifetimes at different fluorescence emissions.

19. The computer readable medium of claim 17, wherein the program instructions cause the computer system to perform the step of:
discriminating between bio-warfare agents and non pathogenic aerosols.

20. The computer readable medium of claim 16, wherein the program instructions cause the computer system to perform the steps of:
generating a second pseudo-random code for modulating an emission of at least one infrared wavelength from an infrared light source; and
controlling the infrared light source for emission of the at least one wavelength from the infrared light source at the second pseudo-random code.

21. The computer readable medium of claim 20, wherein the program instructions cause the computer system to perform the step of:
determining a particle size of the airborne agents by comparison of a backscattered signal from the at least one infrared wavelength of infrared light to the backscattered ultraviolet light signal.

22. The system of claim 1, wherein said controller is configured to compare a particle fluorescence efficiency to the particle size in order to determine an identity of the airborne agents.

23. The method of claim 9, further comprising:
comparing a particle fluorescence efficiency to the particle size in order to determine an identity of the airborne agents.

24. The computer readable medium of claim 16, wherein the program instructions cause the computer system to perform the step of:
analyzing the detected signals for range determination of the airborne agents.

25. The computer readable medium of claim 16, wherein the program instructions cause the computer system to perform the step of:
comparing a particle fluorescence efficiency to the particle size in order to determine an identity of the airborne agents.

* * * * *